United States Patent
Donitzky et al.

(10) Patent No.: US 6,755,817 B1
(45) Date of Patent: Jun. 29, 2004

(54) DEVICE FOR MEDICAL TREATMENT OF THE EYE USING LASER ILLUMINATION

(75) Inventors: Christof Donitzky, Eckental (DE); Joachim Löffler, Heroldsberg (DE)

(73) Assignee: WaveLight LaserTechnologie AG, Erlangen (DE)

( * ) Notice: Subject to any disclaimer, the term of this patent is extended or adjusted under 35 U.S.C. 154(b) by 0 days.

(21) Appl. No.: 10/009,925

(22) PCT Filed: Jun. 6, 2000

(86) PCT No.: PCT/EP00/05197
§ 371 (c)(1),
(2), (4) Date: Dec. 7, 2001

(87) PCT Pub. No.: WO00/76435
PCT Pub. Date: Dec. 21, 2000

(30) Foreign Application Priority Data

Jun. 10, 1999 (DE) .......................... 199 26 473

(51) Int. Cl.$^7$ ............................................. A61B 17/00
(52) U.S. Cl. ................ 606/4; 606/5; 351/204; 351/208; 351/209; 351/210; 351/211; 356/3; 356/3.01; 356/3.03; 356/3.1; 356/3.14; 356/602; 356/606; 356/614; 356/623
(58) Field of Search .................. 606/4–6; 351/200–202, 351/204, 205, 208–212; 356/3, 3.01, 3.03, 3.09, 3.1, 3.11–3.16, 4.01, 9, 601–603, 606–608, 622, 623; 604/294; 128/898

(56) References Cited

U.S. PATENT DOCUMENTS

| | | | |
|---|---|---|---|
| 4,761,071 A | * 8/1988 | Baron ......................... | 351/212 |
| 4,848,340 A | 7/1989 | Bille et al. ................ | 128/303.1 |
| 5,049,147 A | * 9/1991 | Danon ......................... | 606/10 |
| 5,406,074 A | * 4/1995 | Grisell ........................ | 250/221 |
| 5,442,412 A | * 8/1995 | Frey et al. .................. | 351/223 |
| 5,520,679 A | 5/1996 | Lin ................................ | 606/5 |
| 5,684,562 A | * 11/1997 | Fujieda ........................ | 351/212 |
| 6,007,202 A | * 12/1999 | Apple et al. ................. | 351/209 |
| 6,520,958 B1 | * 2/2003 | Shimmick et al. ............ | 606/10 |
| 6,578,962 B1 | * 6/2003 | Amir et al. .................. | 351/209 |

FOREIGN PATENT DOCUMENTS

| | | | |
|---|---|---|---|
| DE | 197 02 335 C1 | 8/1998 | .......... B23K/26/08 |
| DE | 298 09 759 U1 | 9/1998 | ............. F21S/1/02 |
| EP | 0 765 648 A2 | 4/1997 | ............. A61F/9/00 |
| WO | WO 99/20174 | 4/1999 | ............. A61B/3/14 |

OTHER PUBLICATIONS

Marshall, Gerald F.; "Scanner Refinements Inspire New Uses"; Laser Focus World; Jun. 1994; p. 57.

Mans, Fabrice et al.; "Optical Profilometry of Poly (Methylemethacrylate) Surfaces After Reshaping with a Scanning Photorefractive Keratectomy (SPRK) System"; Applied Optics; vol. 35, No. 19; Jul. 1, 1996; pp. 3338–3346.

Gobbi, Pier Giorgio PhD et al.; "Automatic Eye Tracker for Excimer Laser Photorefractive Keratectomy"; Supplemental to Journal of Refractive Surgery; vol. 11; May/Jun. 1995; pp. S337–S342.

* cited by examiner

*Primary Examiner*—Linda C. M. Dvorak
*Assistant Examiner*—Ahmed M. Farah
(74) *Attorney, Agent, or Firm*—Haynes and Boone, LLP

(57) ABSTRACT

A device for the medical treatment of the eye with laser radiation uses auxiliary radiation for determining the eye position. With the aid of the auxiliary radiation, pictures are taken by means of a solid state image camera for determining eye movements and for causing the laser treatment radiation to follow accordingly. Infrared radiation sources, which are arranged in a triangle above the eye to be treated, are used for the auxiliary radiation.

3 Claims, 2 Drawing Sheets

DEVICE FOR MEDICAL TREATMENT OF THE EYE USING LASER ILLUMINATION

CROSS-REFERENCE TO RELATED APPLICATION

Not applicable

STATEMENT REGARDING FEDERALLY SPONSERED RESEARCH OR DEVELOPMENT

Not applicable

REFERENCE TO A "SEQUENCE LISTING", A TABLE OR A COMPUTER PROGRAM LISTING APPENDIX SUBMITTED ON COMPACT DISC

Not applicable

BACKGROUND OF THE INVENTION

The present invention relates to a device for the medical treatment of and/or operation on the eye with laser radiation making use of auxiliary radiation for determining the eye position.

Such a device can especially be used for the so-called PRK (photorefractive keratectomy), i.e. a method of correcting a defective vision of the human eye in the case of which especially the cornea is re-shaped. The device according to the present invention is particularly suitable for the so-called LASIK method where a small flap (lid) is first cut into the epithelium, Bowman's membrane and stroma and opened up, the PRK being then carried out in the stroma.

In the laser treatment of the human eye, the use of various lasers is known; in connection with the present invention these lasers are in particular excimer lasers (having a wavelength of e.g. 193 nm) and also Er:YAG solid state lasers.

In the case of PRK (especially LASIK) material of the cornea is ablated. The ablation is a function of the energy density (energy per unit area) of the laser beam impinging on the cornea. Different techniques for forming and controlling the beam are known, e.g. the so-called slit scanning in the case of which the radiation is guided over the area to be treated by means of a moving slit, the so-called spot scanning in the case of which a radiation spot having very small dimensions is guided over the area to be ablated, and also the so-called full ablation in the case of which large-area application of the radiation is effected over the whole region to be ablated and the radiation density varies across the beam profile so as to achieve the desired ablation of the cornea. Suitable radiation-control algorithms for the respective methods of controlling the beam are known in the prior art so as to ablate the corneal surface such that the cornea will finally be given the desired radius of curvature.

Spot scanning, which has already been mentioned hereinbefore, uses a laser beam focussed to a comparatively small diameter (0.1–2 mm), said laser beam being directed onto various points of the cornea by means of a beam control unit and successively moved by means of a so-called scanner in such a way that the desired corneal ablation will finally be achieved. For the purpose of PRK, so-called galvanometric scanners can especially be used (cf. the article, G. F. Marshall in LASER FOCUS WORLD, Jun. 1994, p. 57). The present invention refers in particular to the so-called spot scanning executed in the LASIK method.

A special problem arising in connection with PRK and LASIK is the relative positioning of the laser beam and of the eye. A mechanical fixation of the eye is not satisfactory for medical reasons. Hence, the prior art knows a so-called optical fixation in the case of which a so-called fixation beam is used, which is normally coaxial with the material-ablating laser beam. The patient is requested to look precisely at the point defined by the fixation beam so that the eye will always maintain the same position during the whole surgical operation. The patient does, however, not succeed in doing so, at least not with sufficient reliability, so that movements of the eye occur which may seriously impair the whole ablation process.

The prior art knows so-called "eye-trackers"; these are means which detect movements of the eye so that the laser beam used for ablation can then be controlled (caused to follow) in accordance with the eye movements. With regard to the prior art, reference is made to the following documents:

Gobbi, Pier Giorgie et al.: Automatic Eye Tracker for Excimer Laser Photorefractive Keratectomy; Supplement to Journal of Refractive Surgery, Vol. 11, May/June 1995; in addition, Lin, J. T., Ophthalmic Surgery Method Using Non-Contact Scanning Laser, U.S. Pat. No. 5,520,679, May 28, 1996; and Manns, Fabrice, et al., Optical profilometry of poly(methyl-methacrylate) surfaces after reshaping with a scanning photorefractive keratectomy (SPRK) system, periodical APPLIED OPTICS, Vol. 35, No. 19, Jul. 1, 1996.

Furthermore, reference is made to German Utility Model 298 09 759.1. In this German Utility model white light, which is emitted by light-emitting diodes, is used for the auxiliary radiation which serves to determine the eye position for "eye-tracking".

DE 197 02 335 C1 describes a laser system for treating the cornea with means for causing the laser treatment beam to follow when the eye moves relative to a reference axis. An image-recording means (CCD camera) is used for this purpose and auxiliary radiation is used for illuminating the eye for the image-recording process. In accordance with a movement of the eye relative to the reference axis, a control controls a beam control unit, e.g. a galvanometric scanner. A specific dependence with respect to the pulse repetition rate of the laser radiation is suggested for the image sequence rate at which the camera takes pictures. This prior art is here assumed to be known, and used. Summarizing, it can be stated that this prior art teaches that images of the eye are recorded by means of a camera and processed in rapid succession so as to determine movements of the eye. A change in the position of the eye (pupil position) can be determined from successive images (e.g. two successive images), and the ablation laser beam can then be caused to follow in accordance with the eye movement with the aid of suitable beam control means (e.g. the above-mentioned galvanometric scanner).

It follows that at least three different radiations are differentiated in connection with PRK (in particular LASIK). Firstly, the actual laser treatment beam which causes the ablation, secondly, the so-called auxiliary radiation, i.e. the radiation which serves to illuminate the eye so as to detect the eye position e.g. by means of the camera, and, thirdly, optionally, the so-called fixation beam which is stationary and which is intended to cause the patient to fixate always the same point with the eye (the latter is only a special option).

In the prior art, halogen light, which is introduced into the observation ray path by means of a bundle of fibres, is used for illuminating the eye. Also the use of a ring lamp or the coaxial coupling in of the illumination radiation via a surgical microscope is part of the prior art. Flexible swan necks for positioning the illumination light for illuminating the foreground of the eye, especially the cornea, are known as well, so that the physician can selectively adjust the light for an optimum observation of the eye as a whole. The halogen lamps and xenon lamps used in the prior art are improvable with respect to the strain on the patient as well as with respect to the illumination quality for the physician carrying out the treatment.

When, especially during spot scanning for LASIK, pictures of the iris and of the pupil are taken by means of a camera system for determining the eye position and when the centre of gravity of the pupil is then calculated (on-line), a high contrast between pupil and iris is necessary for optimum recognition of the pupil. It turned out that the auxiliary radiation is very important with respect to its angles of incidence, wavelengths, etc. for achieving good results when the eye position is being determined.

It is therefore the object of the present invention to further develop a device for the medical treatment of the eye of the type mentioned at the beginning, in such a way that reliable results are achieved when the eye position is being determined, especially when the system is used for different eyes (patients) and under different conditions.

BRIEF SUMMARY OF THE INVENTION

Solutions provided for this task in accordance with the present invention are described in the claims.

The present invention is based on the finding that particularly good measurement results with regard to the eye position will be achieved when at least two infrared radiation sources are used, the radiations of these infrared radiation sources extending at an angle of 30 to 70°, preferably between 40 and 60°, to the optical axis of the laser treatment radiation. Although the optical axis of the laser treatment radiation varies slightly during scanning, it can essentially be considered to be fixed in space; in particular, it can essentially be equated with the optical axis of the eye at rest.

According to a further variant of the invention, at least three radiation sources are provided for the auxiliary radiation, the radiations of these radiation sources extending at an angle of 30 to 70°, preferably between 40 and 60°, to the optical axis of the treatment radiation. Also in this case, the use of infrared radiation sources is specially preferred, these infrared radiation sources being preferably used in the form of light-emitting diodes (LEDs), in particular LEDs having a wavelength of approx. 810 nm.

The above-mentioned radiation sources themselves can each be composed of a large number of LEDs. A "radiation sources" in the sense of this application is then a system comprising a plurality of LEDs which are firmly connected to one another physically and the composite radiation of which is directed onto the eye from substantially the same direction.

A specially preferred embodiment is so conceived that the radiation sources define a triangle below which the eye to be treated can be positioned. The above-mentioned triangle can be positioned in a horizontal plane or in a plane which is slightly inclined relative to the horizontal. The terms "horizontal" and "vertical" are here used in the usual sense, i.e. it is assumed that the patient, who lies on his back, is horizontally oriented. Since electromagnetic radiation can, for the present purposes, be considered to be independent of gravitation and since also the patient can, in principle, be oriented in an arbitrary manner, the terms "horizontal" and "vertical" are here used only to give a general picture; it is assumed that the patient lies in the usual way and that his head is oriented such that the eyes face upwards.

When at least three radiation sources are used for the auxiliary illuminating radiation, a preferred embodiment of the invention is so conceived that the radiations of at least two radiation sources extend at an acute angle relative to one another towards the eye to be treated. This acute angle can e.g. be in the range of from 30 to 70°, preferably in the range of from 40 to 60°. A preferred embodiment of this variant of the invention is so conceived that, when projected onto a horizontal plane, the radiation of a third radiation source extends approximately in the direction of the angle bisector of said acute angle between the two other beams.

BRIEF DESCRIPTION OF SEVERAL VIEWS OF THE DRAWINGS

In the following, one embodiment of the present invention is explained in detail making reference to the drawings.

DETAILED DESCRIPTION OF THE INVENTION

Figure 1:
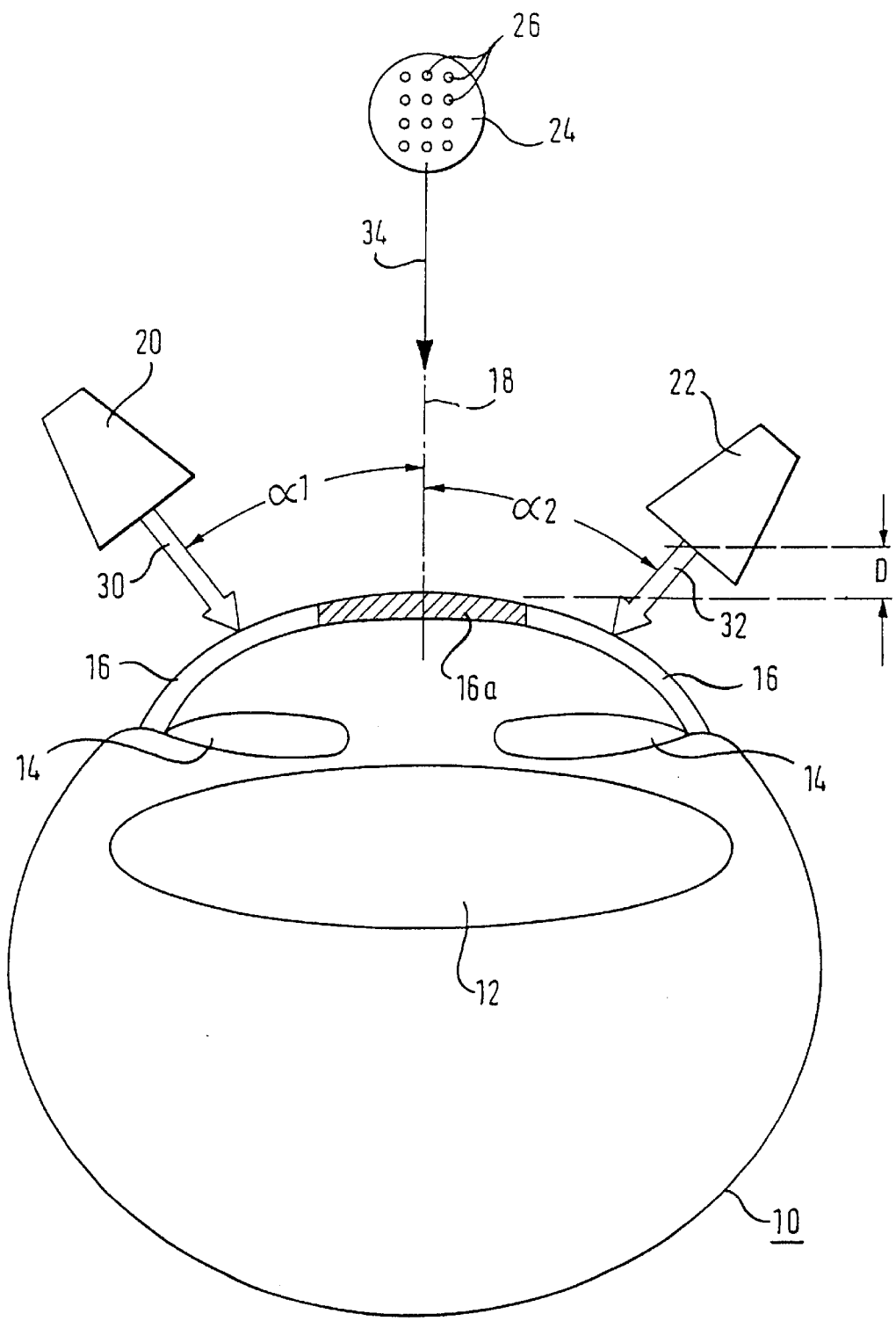
FIG. 1 shows schematically a vertical section through an eye to be treated and the arrangement of a plurality of radiation sources for the auxiliary radiation.

FIG. 1 shows an eye 10 to be treated comprising a lens 12, an iris 14 and a cornea 16. The corneal area 16a to be treated with laser radiation (e.g. excimer laser radiation having a wavelength of 193 nm) is hatched in FIG. 1.

Figure 2:
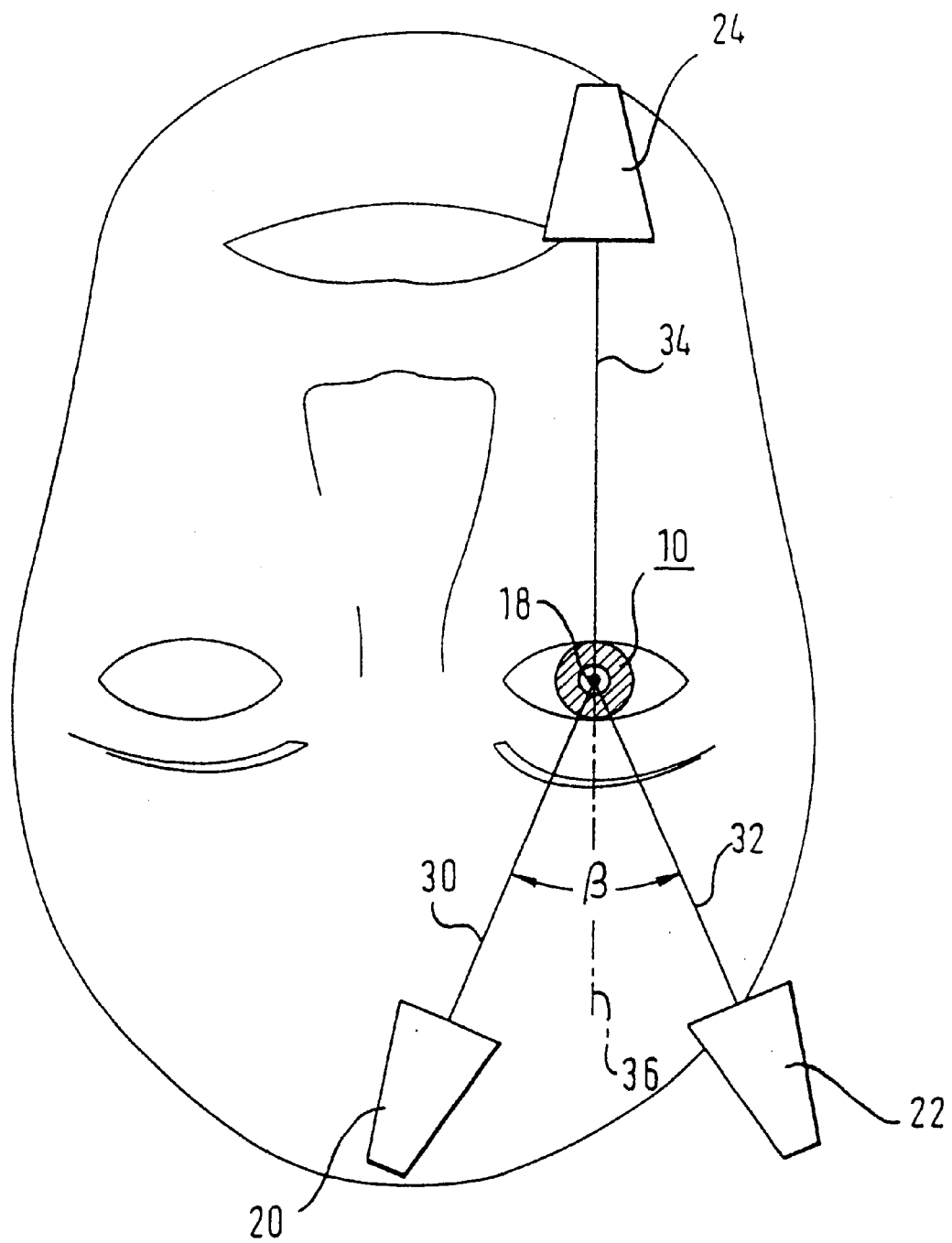
FIG. 2 shows a top view of the device of FIG. 1 with three radiation sources for the auxiliary radiation.

FIG. 1 is a vertical section through the eye 10. FIG. 2 shows a top view of the eye 10 to be treated and the arrangement of three radiation sources 20, 22, 24 for the auxiliary radiation used for determining the eye position. Neither the camera system nor the actual laser treatment beam are shown separately in the figures. They correspond to the above-mentioned prior art. The description following hereinbelow is therefore limited to the auxiliary radiation and its arrangement with respect to the eye.

Each individual radiation source 20, 22, 24 consists of a plurality of individual light-emitting diodes (LEDs) 26. The LEDs emit radiation in the infrared region having a wavelength of 810 nm. For the camera (not shown) a daylight filter is used. The camera used can e.g. be a black-and-white camera. For achieving good measurement results with respect to the eye position, it is important to obtain a high contrast between the pupil (dark) and the iris (bright). This is achieved by means of the auxiliary radiation of the radiation sources 20, 22, 24, which is described here.

In the embodiment shown, each radiation source 20, 22, 24 comprises twelve individual IR LEDs which are interconnected so as to define an array of 3×4 LEDs. FIG. 1 shows one of the radiation sources (radiation source 24) so that the individual LEDs 26 can be seen. The two outer LED rows, which each consist of four LEDs, have e.g. a radiation angle of ±8°, whereas the inner row, which comprises four LEDs, has a radiation angle of ±20°. The radiation angle referred to corresponds approximately to the divergence angle of the radiation lobe. The above-mentioned choice of radiation angles permits mixing of the radiation within an array; this proved to be advantageous with regard to a shadow-free and homogeneous illumination. A choice of different radiation angles within one radiation source is preferably used in the case of all three radiation sources 20, 22, 24.

The radiations produced by the individual LEDs are combined so as to form one composite beam 30, 32, 34. The resultant beams can be seen from FIGS. 1 and 2 as far as their positioning relative to one another and relative to the eye 10 to be treated is concerned.

In the horizontal representation according to FIG. 2, the actual laser treatment beam (not shown separately) extends at right angles to the plane of the drawing; its axis is designated by reference numeral 18. The illuminating beams (auxiliary beams) 30, 32, 34 extend slightly inclined to the horizontal plane and at an angle α relative to the axis 18 of the laser treatment beam. FIG. 1 shows the angles between the illumination beams 30, 32 and the laser treatment beam 18, viz. the angles $\alpha_1$ and $\alpha_2$. The above applies accordingly to the third radiation source 24. The angles $\alpha_1$, $\alpha_2$ are in a range of 40 to 60°. The distance D between the exit aperture of the illuminating beams 30, 32, 34 and the top tangential plane of the cornea to be treated is approx. 20 to 150 mm, preferably approx. 30 to 100 mm.

It will be particularly advantageous to achieve light admission of the IR light outside of the treatment zone 16a by means of the above-described oblique incidence of the illuminating radiation. This will guarantee that no substantial change in the conditions for the illuminating radiation will occur during the treatment. During the treatment, the transmission of the cornea may change drastically within the treatment zone 16a. In the case of the illumination system described and shown in FIGS 1 and 2, such a change does not have any substantial influence on the illuminating radiation and, consequently, the determination of the eye position. In addition, disturbing but unavoidable reflections of the IR illuminating radiation on the corneal surface are displaced into the peripheral area of the cornea where they will not disturb the evaluation of the determined contour of the pupil.

FIGS. 1 and 2 also show a preferred arrangement of the radiation sources relative to one another. Two radiation sources 20, 22 are arranged such that the illuminating beams 30, 32 emitted by them form an angle p when projected onto a horizontal plane. The angle β is an acute angle, preferably in the range of from 25 to 70°, better still in the range of from 35 to 65°. The third radiation source 24 is then arranged in such a way that its radiation 34 extends approximately in the area of the angle bisector 36 of the angle β between the two other beams. This will lead to optimum illumination and best results with regard to the determination of the eye position when the camera images are being evaluated.

What is claimed is:

1. A device for determining the position of an eye during medical treatment using laser radiation extending along an optical axis from a medical treatment laser, comprising:

radiation sources consisting of three infrared radiation sources each for generating an auxiliary radiation used for determining the position of the eye, wherein the three auxiliary radiations extend at an angle of 30 to 70° to the optical axis of the medical treatment laser the three auxiliary radiations define a triangle in such a way that two of the three auxiliary radiations extend at an acute angle relative to one another towards the eye, and that, when projected onto a horizontal plane transverse to the optical axis, the remaining of the three auxiliary radiations extends in the direction of the angle bisector of the acute angle.

2. A device according to claim 1, characterized in that the angle between the radiations and the optical axis is in the range of from 40° to 60°.

3. A device according to claim 1, wherein said triangle is a nonequilateral triangle.

* * * * *

UNITED STATES PATENT AND TRADEMARK OFFICE
CERTIFICATE OF CORRECTION

PATENT NO.   : 6,755,817 B1
DATED        : June 29, 2004
INVENTOR(S)  : Christof Donitzky et al.

It is certified that error appears in the above-identified patent and that said Letters Patent is hereby corrected as shown below:

Title page,
Item [54], Title, the word "ILLUMINATION" should be replaced with
-- RADIATION --;

Column 3,
Line 3, the word "comea" should be replaced with -- cornea --;
Line 51, the word "sources"" should be replaced with -- source" --

Signed and Sealed this

Fifth Day of October, 2004

JON W. DUDAS
*Director of the United States Patent and Trademark Office*